(12) United States Patent
Ponmudi et al.

(10) Patent No.: US 11,172,918 B2
(45) Date of Patent: Nov. 16, 2021

(54) ORTHOPEDIC TOOLS FOR IMPLANTATION

(71) Applicant: GLOBUS MEDICAL, INC., Audubon, PA (US)

(72) Inventors: Varun Ponmudi, Scotch Plains, NJ (US); Edward Karpowicz, Sewell, NJ (US)

(73) Assignee: Globus Medical Inc., Audubon, PA (US)

( * ) Notice: Subject to any disclaimer, the term of this patent is extended or adjusted under 35 U.S.C. 154(b) by 196 days.

(21) Appl. No.: 16/529,840

(22) Filed: Aug. 2, 2019

(65) Prior Publication Data

US 2019/0350572 A1 Nov. 21, 2019

Related U.S. Application Data

(63) Continuation of application No. 14/519,961, filed on Oct. 21, 2014, now Pat. No. 10,426,454.

(51) Int. Cl.
*A61B 17/02* (2006.01)
*A61B 17/70* (2006.01)

(52) U.S. Cl.
CPC ........ *A61B 17/025* (2013.01); *A61B 17/0206* (2013.01); *A61B 17/7074* (2013.01); *A61B 17/7077* (2013.01); *A61B 2017/0256* (2013.01)

(58) Field of Classification Search
CPC ... A61B 17/02; A61B 17/025; A61B 17/0206; A61B 17/0218
See application file for complete search history.

(56) References Cited

U.S. PATENT DOCUMENTS

| | | |
|---|---|---|
| 5,944,658 A | 8/1999 | Koros et al. |
| 6,139,493 A | 10/2000 | Koros et al. |
| 2004/0230191 A1 | 11/2004 | Frey et al. |
| 2007/0055240 A1 | 3/2007 | Matthis et al. |
| 2007/0100212 A1 | 5/2007 | Pimenta et al. |
| 2009/0036746 A1 * | 2/2009 | Blackwell .......... A61B 17/0206 600/219 |
| 2009/0275952 A1 | 11/2009 | Lawson et al. |
| 2012/0303034 A1 | 11/2012 | Woolley et al. |
| 2014/0012269 A1 | 1/2014 | Bass |
| 2014/0066718 A1 | 3/2014 | Fiechter et al. |
| 2014/0194697 A1 | 7/2014 | Seex |

FOREIGN PATENT DOCUMENTS

| | | |
|---|---|---|
| JP | 2007014787 A | 1/2007 |
| JP | 2008509763 A | 4/2008 |
| JP | 2014050714 A | 3/2014 |

* cited by examiner

*Primary Examiner* — Si Ming Ku

(57) ABSTRACT

The present application is generally directed to improved instruments and instrument features for distraction and tissue retraction. In particular, the present application is directed to distraction blades and wide blocking blades that can be used together, or individually, to assist in the distraction of bone and the retraction of tissue during a surgical procedure, such as a spinal fusion procedure.

20 Claims, 17 Drawing Sheets

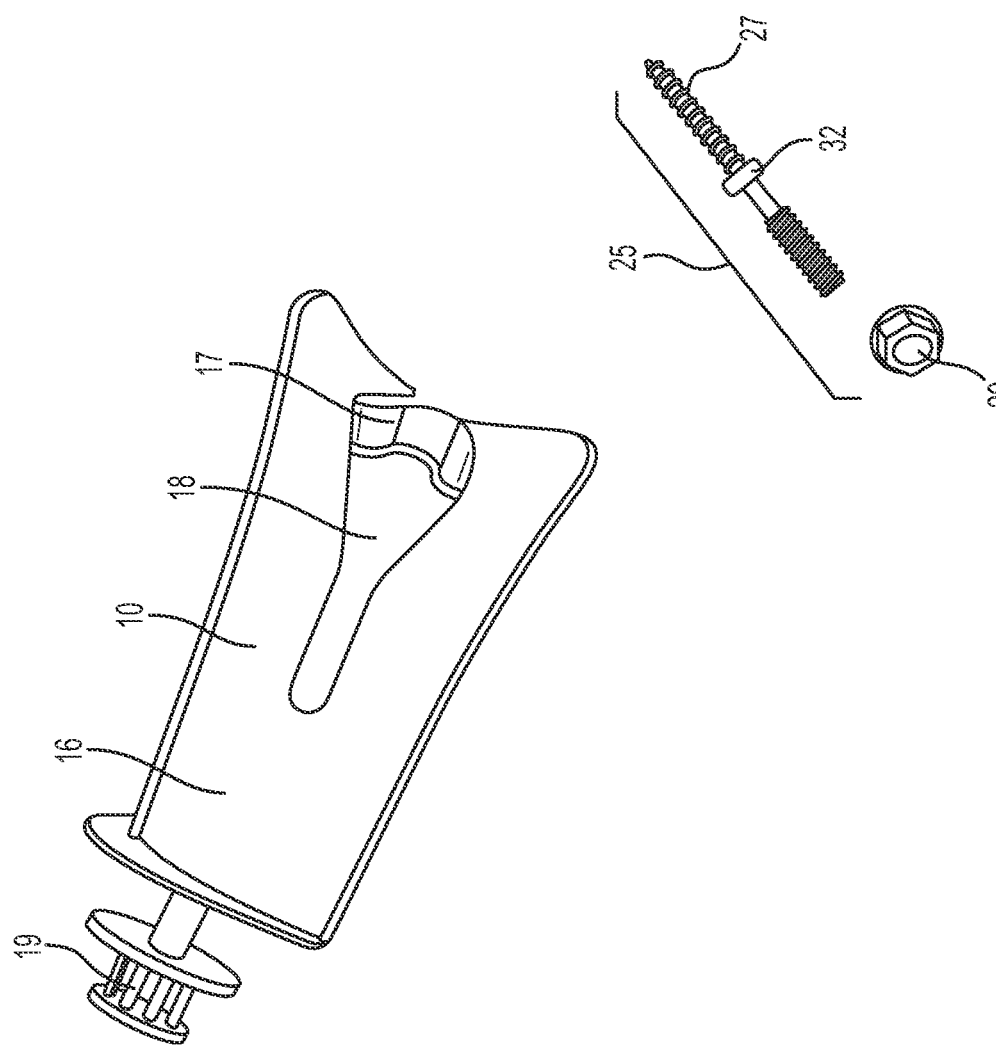

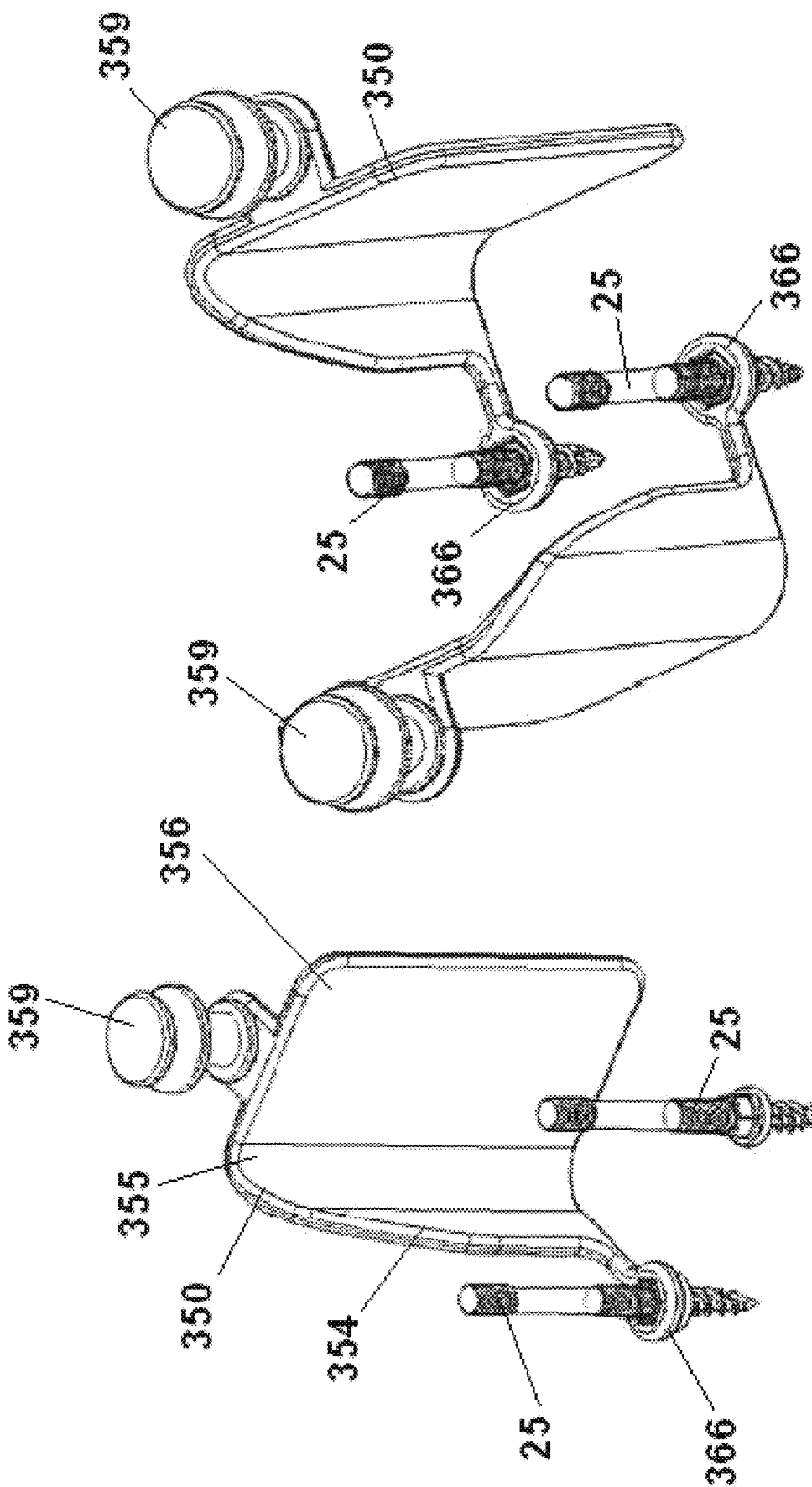

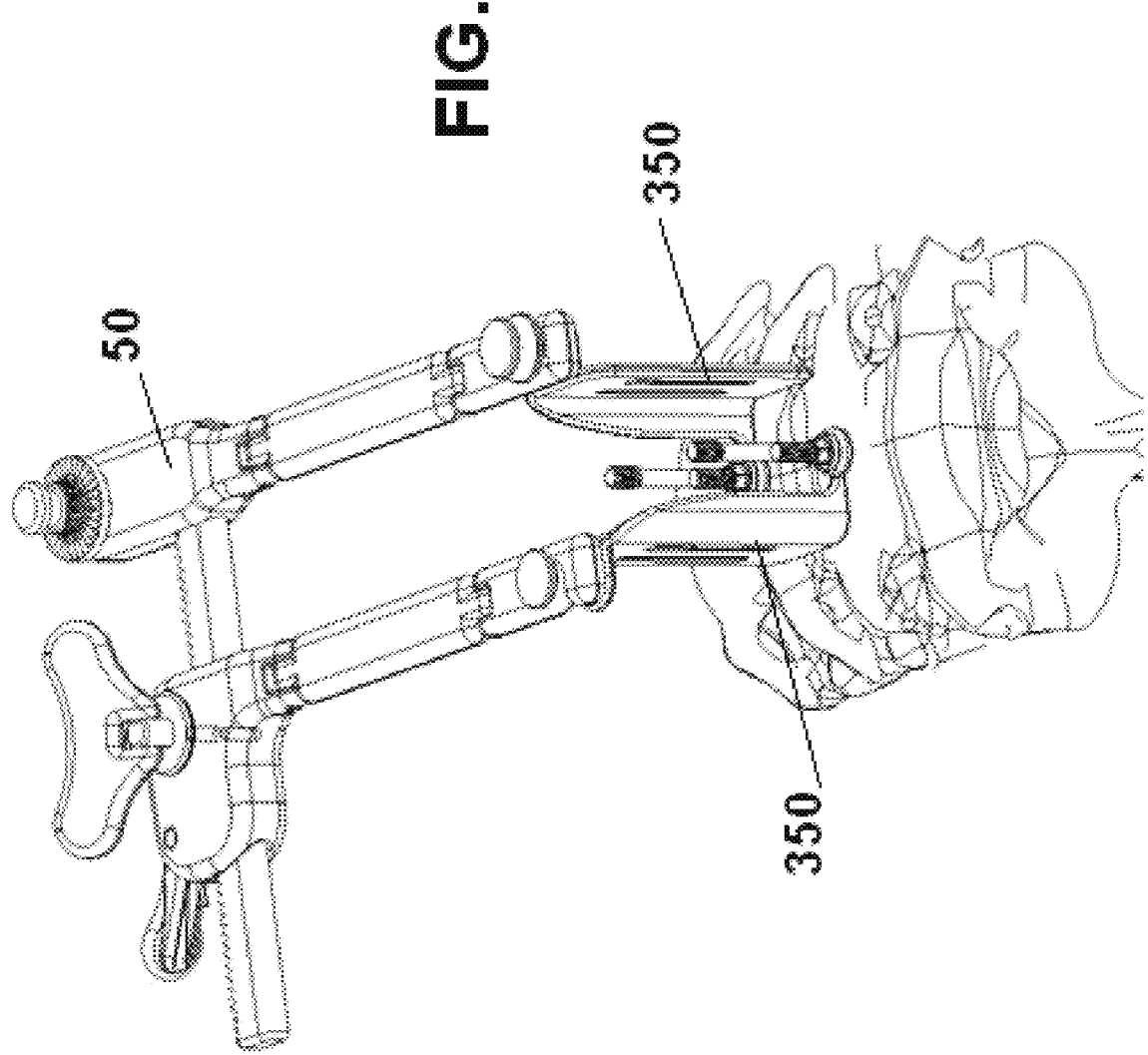

ORTHOPEDIC TOOLS FOR IMPLANTATION

CROSS REFERENCE TO RELATED APPLICATION

This application is a continuation of U.S. application Ser. No. 14/519,961, filed on Oct. 21, 2014 (published as U.S. Pat. Pub. No. 2016-0106408), which is hereby incorporated by reference in its entirety for all purposes.

FIELD OF THE INVENTION

The present application is generally directed to improved instruments and instrument features for distraction and tissue retraction.

BACKGROUND

Spinal fusion procedures are performed on patients to treat lower back pain caused by degenerated discs. During spinal fusion procedures, a surgeon restores a disc space back to its original height before inserting an interbody fusion device and graft material into the disc space. To accomplish this, a surgeon uses a distraction instrument to separate adjacent bones. To access the surgical site, a surgeon retracts tissue. The tissue retraction is performed by a retraction instrument that is separate from the distraction instrument.

There is a need for tools to better serve the purpose of both bone distraction and tissue retraction.

SUMMARY OF THE INVENTION

The present application is generally directed to improved instruments and instrument features for distraction and tissue retraction. In some embodiments, an orthopedic system comprises a first bone pin, wherein the first bone pin comprises a lower threaded portion and an upper threaded portion; a first wide blocking blade delivered over the first bone pin, wherein the first wide blocking blade comprises at least two blocking panels; a first distraction blade delivered over the first bone pin, wherein the first distraction blade includes a slot for receiving the first bone pin therein; a second bone pin, wherein the second bone pin comprises a lower threaded portion and an upper threaded portion; a second wide blocking blade delivered over the second bone pin, wherein the second wide blocking blade comprises at least two blocking panels; a second distraction blade delivered over the second bone pin, wherein the second distraction blade includes a slot for receiving the second bone pin therein; and a frame attached to at least one of either: (i) the first distraction blade and the second distraction blade or (ii) the first wide blocking blade and the second wide blocking blade.

In other embodiments, the orthopedic system comprises a first bone pin; a first wide blocking blade delivered over the first bone pin; a first distraction blade delivered over the first bone pin, wherein the first distraction blade includes a slot for receiving the first bone pin therein; a second bone pin; a second wide blocking blade delivered over the second bone pin; a second distraction blade delivered over the second bone pin, wherein the second distraction blade includes a slot for receiving the second bone pin therein; and a frame attached to at least one of either: (i) the first distraction blade and the second distraction blade or (ii) the first wide blocking blade and the second wide blocking blade.

In other embodiments, the orthopedic system comprises a first bone pin; a first wide blocking blade delivered over the first bone pin; a second bone pin; a second wide blocking blade delivered over the second bone pin; and a frame attached to the first wide blocking blade and the second wide blocking blade.

BRIEF DESCRIPTION OF THE DRAWINGS

FIG. 4 shows a distraction blade separated from an integrated bone pin in accordance with some embodiments.

FIGS. 16-21 show a method of assembly of one or more wide blocking blades in conjunction with one or more distraction blades in accordance with some embodiments.

FIG. 22 shows a pair of wide blocking blades in use with a frame in accordance with some embodiments.

DETAILED DESCRIPTION OF THE ILLUSTRATED EMBODIMENTS

The present application is generally directed to improved instruments and instrument features for distraction and tissue retraction. In particular, the present application describes spine surgery instruments that are capable of both distraction and tissue retraction, thereby advantageously removing the need to use multiple instruments during spinal procedures.

During spinal fusion procedures, a surgeon restores a disc space back to its original height before inserting an interbody fusion device and graft material into the disc space. To accomplish this height restoration, a surgeon uses a distraction instrument to separate adjacent bones. In order to access the surgical site to perform the distraction, a surgeon must retract tissue to provide a pathway to the site. The tissue retraction is performed using a retraction instrument that is typically separate from the distraction instrument.

One common type of spine procedure is an ACDF procedure. In the last ten years, the number of ACDF procedures has more than doubled, with the rate of success being quite high. Despite the high success rate, improvements are still needed. Studies have found that the incidence of dysphagia after ACDF can be quite high, with reports showing that up to 47% of patients experience short-term swallowing dysfunction, with possibly more going unreported. It is believed that the presence of dysphagia is related to the force applied by ACDF retractors against surrounding soft tissue, dissection of the longus coli muscle, as well as intubation tubing. Additional concerns arise during the ACDF procedures themselves, when delays may occur from constant shifting of the typical self-retaining retractors and difficulty in visibility arises from the clutter of retractor frames used alongside separate distracters, all within what is intended to be the smallest incision required.

The present application is directed to instruments and instrument features that reduce the likelihood of dysphagia and other side-effects that may occur during ACDF procedures. The instruments described herein can be used to both retract tissue and distract vertebral bodies to their original height, thereby reducing the need to use separate instruments and increasing visibility to a surgical site. By providing instruments that can both retract tissue and distract vertebrae, tissue can be protected during the distraction process, thereby reducing the risk of dysphagia to a patient. While the instruments described herein are illustrated with respect to an ACDF procedure, one skilled in the art will appreciate that the instruments can be applied to other vertebral members as well, including in the thoracic, lumbar and sacral regions.

Figure 1:
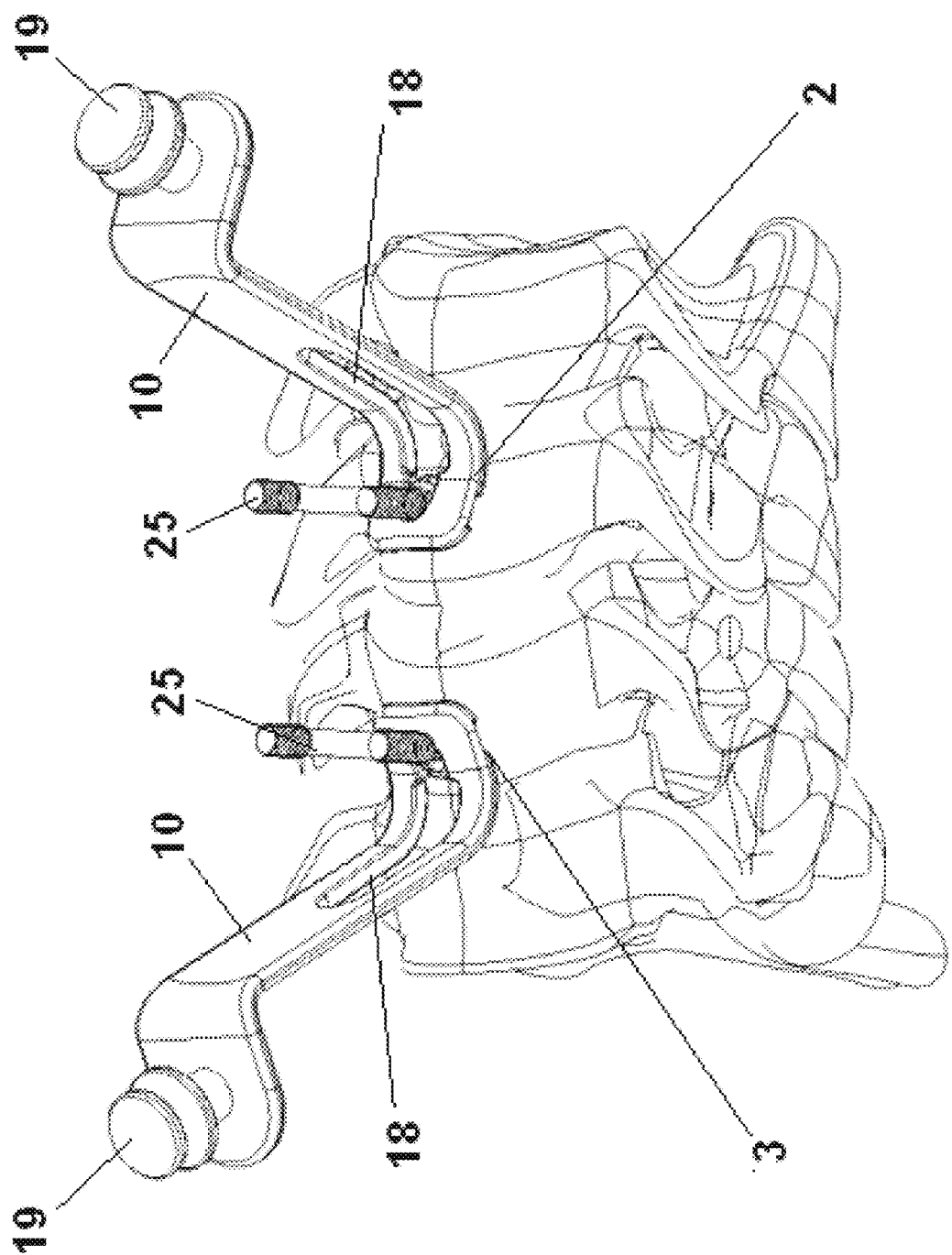
FIG. 1 shows a system including pair of distraction blades attached to vertebral bodies in accordance with some embodiments.
Figure 2:
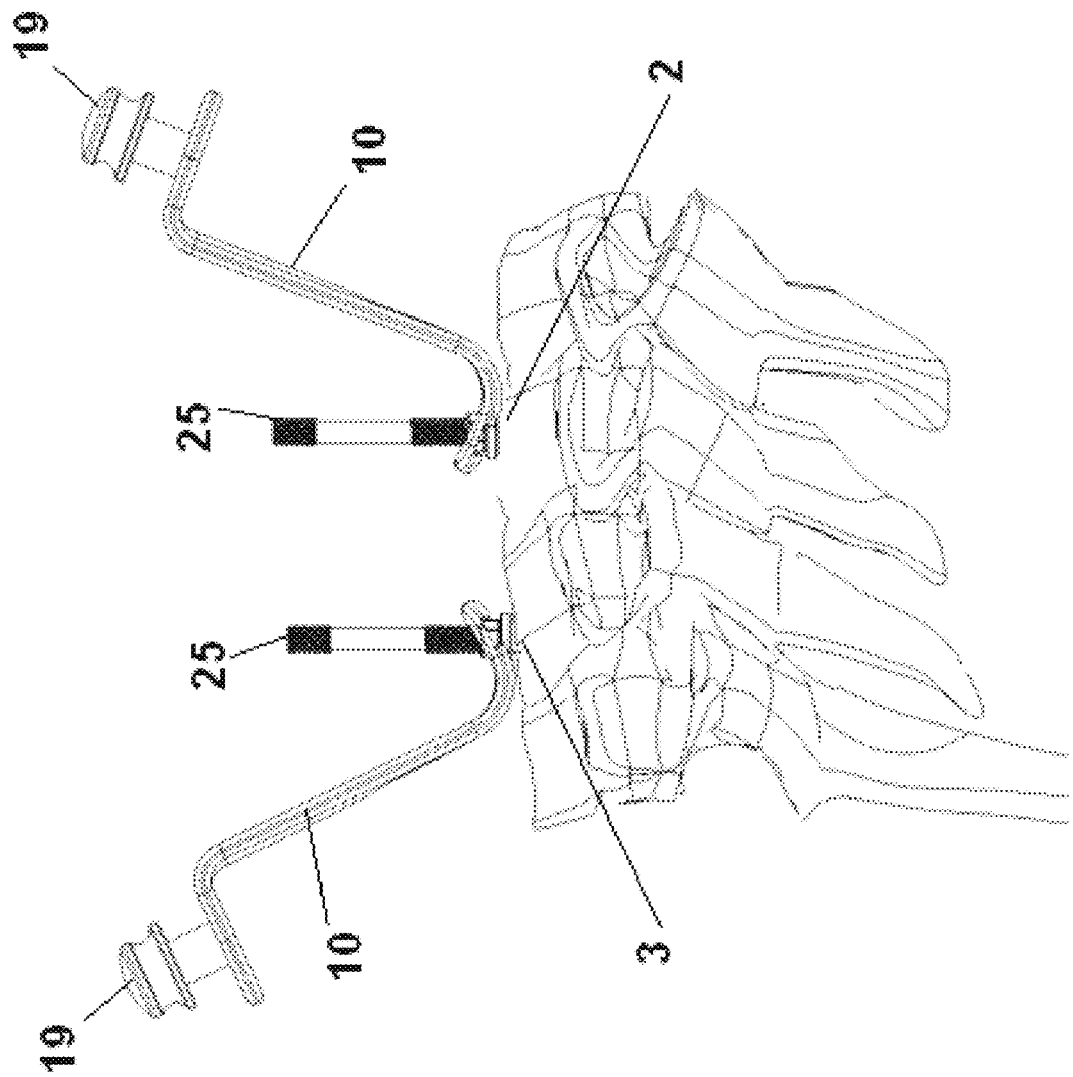
FIG. 2 shows a different view of the distraction blades of FIG. 1.

FIGS. 1 and 2 show different views of a surgical system comprising a pair of novel distractor blades that are capable of both bone distraction and tissue retraction in accordance with some embodiments. Each of the distraction blades 10 is associated with an integrated threaded bone pin 25 that is positioned through a bone member. As shown in FIG. 1, a first bone pin 25 is inserted into a first or upper vertebra 2, while the other bone pin 25 is inserted into a second or lower vertebra 3. In some embodiments, the installation of the bone pins 25 into the bone members can occur prior to delivering the distraction blades 10 to the bone pins 25. With the bone pins 25 in place, the distraction blades 10 can be positioned downwardly over and around the bone pins 25 via slots 18. The distraction blades 10 can rest on a washer, flange, protrusion or shelf feature 32 (shown in FIG. 7) of the bone pins 25, prior to securing the distraction blades to the bone pins 25 via locking nuts 29 (also shown in FIG. 7) in preparation for distraction. If some embodiments, the locking nuts 29 can be applied loosely to secure the distraction blades 10 to the bone pins 25, thereby allowing angulation and wanding to provide more room for additional instrumentation during the surgical procedure. Advantageously, the distraction blades 10 retract tissue as they are being inserted toward the bone pins 25, and can continue to retract tissue once secured to the bone pins.

Figure 8A:
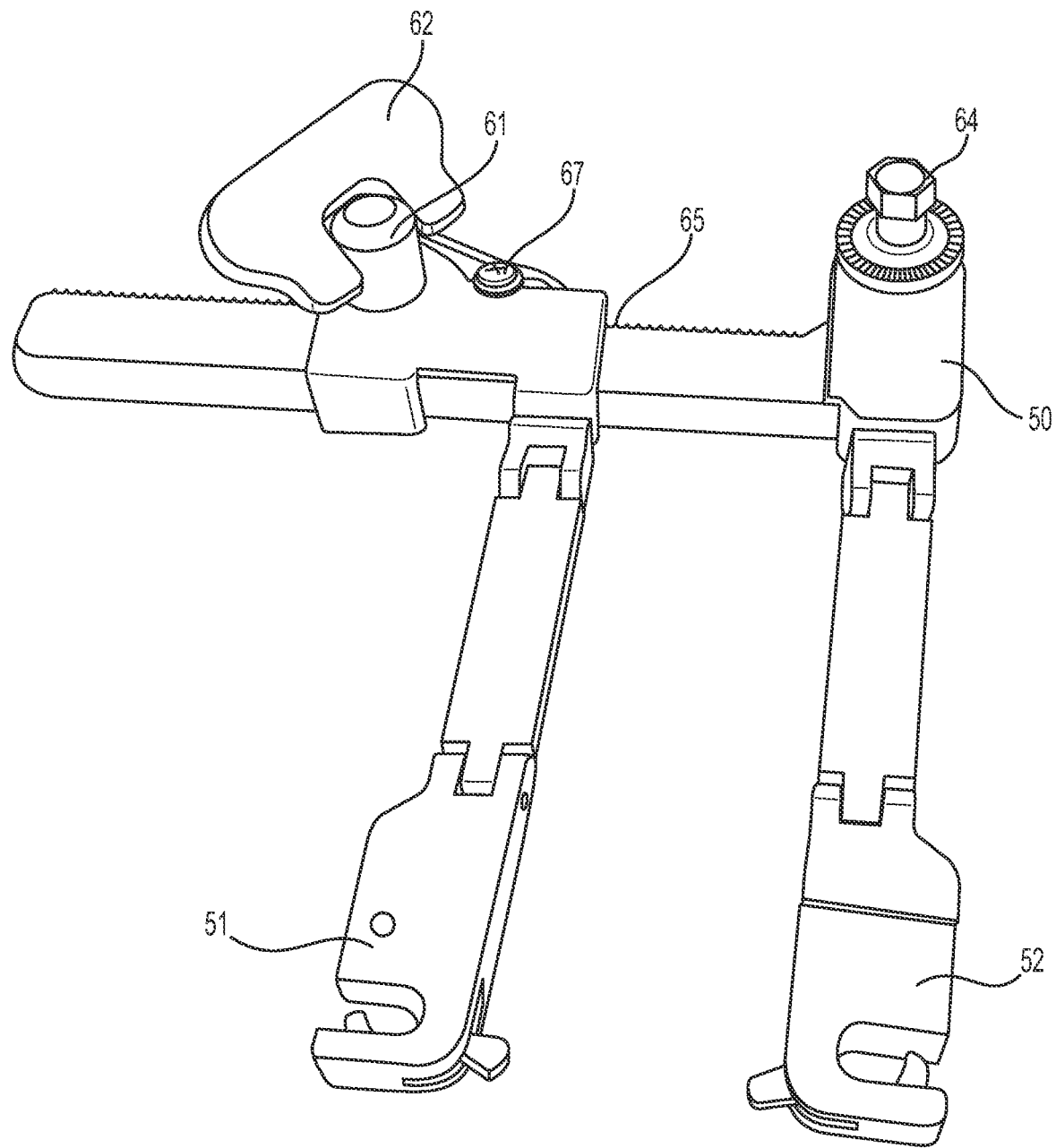
FIGS. 8A and 8B show different views of a frame in accordance with some embodiments.
Figure 8B:
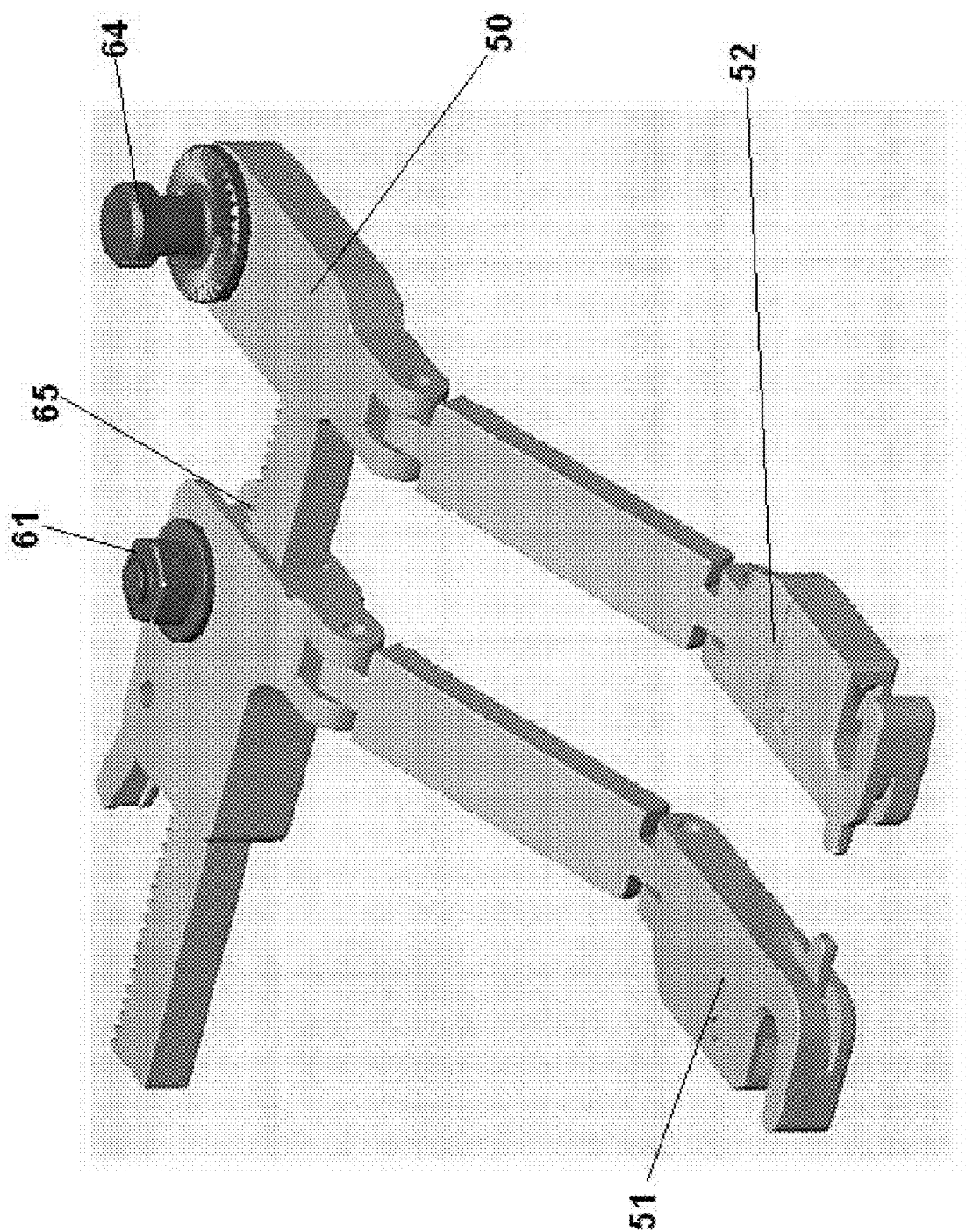

With the two distraction blades 10 in place with the integrated bone pins 25 as shown in FIGS. 1 and 2, the distraction blades 10 are capable of distracting the adjacent vertebral bodies to restore disc height. Distraction can occur via hand or via instrument. In some embodiments, one or more instruments for distraction can be attached to the attachment portions 19 that are provided on each of the distraction blades 10. In some embodiments, a frame 50, as shown in FIGS. 8A and 8B, can be attached to the distraction blades 10, with a first arm 51 of the frame 50 attached to a first distraction blade 10 and a second arm 52 attached to a second distraction blade 10. The frame 50 can include a mechanism (e.g., a ratcheting mechanism) that can help the distraction blades 10 to distract the adjacent vertebral bodies. As such, the two distraction blades 10 can advantageously be used for distraction, while continuing to retract tissue, thereby reducing the need for separate distraction and retraction instruments. Individual components of the surgical system including the distraction blades and integrated pins are discussed in more detail below.

Figure 3:
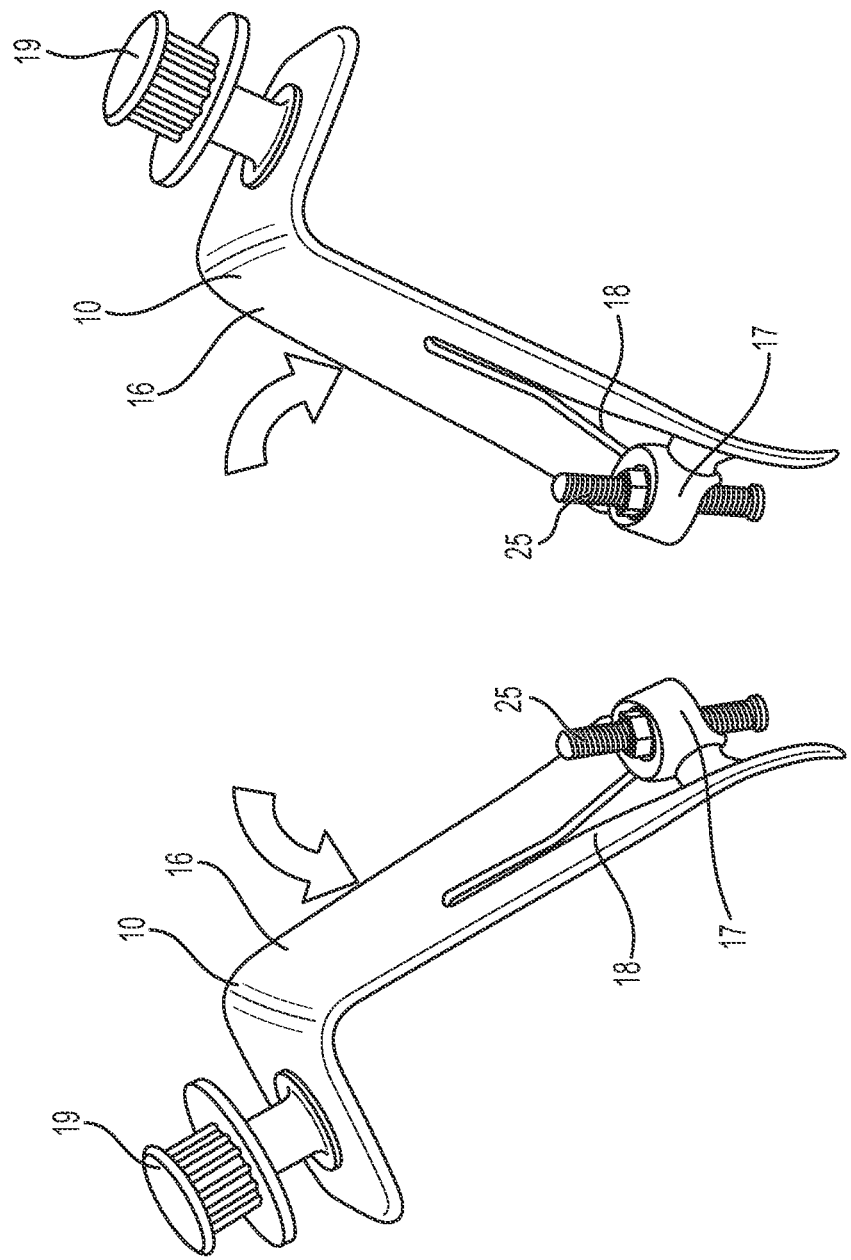
FIG. 3 shows a system including a pair of distraction blades with integrated bone pins in accordance with some embodiments.

FIG. 3 shows a system including a pair of distraction blades with integrated bone pins in accordance with some embodiments. Each of the distraction blades 10 includes a body 16 having an upper portion and a lower portion. The upper portion of the body 16 includes a flattened section from which an attachment portion 19 extends or protrudes. The attachment portion 19 is capable of attachment to a frame or other instrument for stabilization, retraction and/or distraction. The upper portion of the body 16 slopes downwardly into a flared lower portion that includes an opening or slot for accepting a bone pin 25 therethrough. In the present embodiment, a hoop or ring element 17 (shown better in FIGS. 4 and 6) extends outwardly from the flared lower portion. The ring element 17 can be designed to both receive the integrated bone pin 25 and rest on the bone pin's shelf feature 32, shown in FIG. 7.

Once a distraction blade 10 receives a bone pin 25, a locking nut 29 (shown in FIG. 7) can be downwardly threaded onto the bone pin 25 to secure the distraction blade 10 and bone pin 25. In some embodiments, the locking nut 29 is downwardly threaded but not tightened completely so that the distraction blade 10 is capable of angling or wanding. In other embodiments, the locking nut 29 is downwardly threaded and tightened completely so that the distraction blade 10 is fixed and not capable of wanding. In some embodiments involving a pair of distraction blades 10, either blade can be fixed and/or capable of wanding. Regardless of whether the locking nut 29 is threaded downwardly and tightened completely or partially, the distraction blade 10 will be attached to the bone pin 25. At that point, when two or more distraction blades 10 are attached to their respective bone pins, a distraction instrument can be attached to both so as to distract a first vertebral body from another.

FIG. 4 shows a distraction blade separated from an integrated bone pin in accordance with some embodiments. From this view, one can see how the body 16 of the distraction blade 10 has an upper portion with a flattened surface from which an attachment portion 19 extends, and a lower flared out portion that extends from the upper portion. The lower flared out portion tapers outwardly such that a distal most end of the distraction blade 10 is the widest portion of the blade 10. The flared shape of the distraction blade 10 is unique and allows it to contour to the vertebral body, which allows for more secure positioning with the integrated bone pin 25. As shown in FIG. 4, the slot 18 that extends through the body 16 of the blade can also have a flared portion that gets wider toward a more distal end of the distraction blade 10. This widening of the slot 18 advantageously allows the pin 25 to be easier received within the distraction blade 10.

Figure 7:
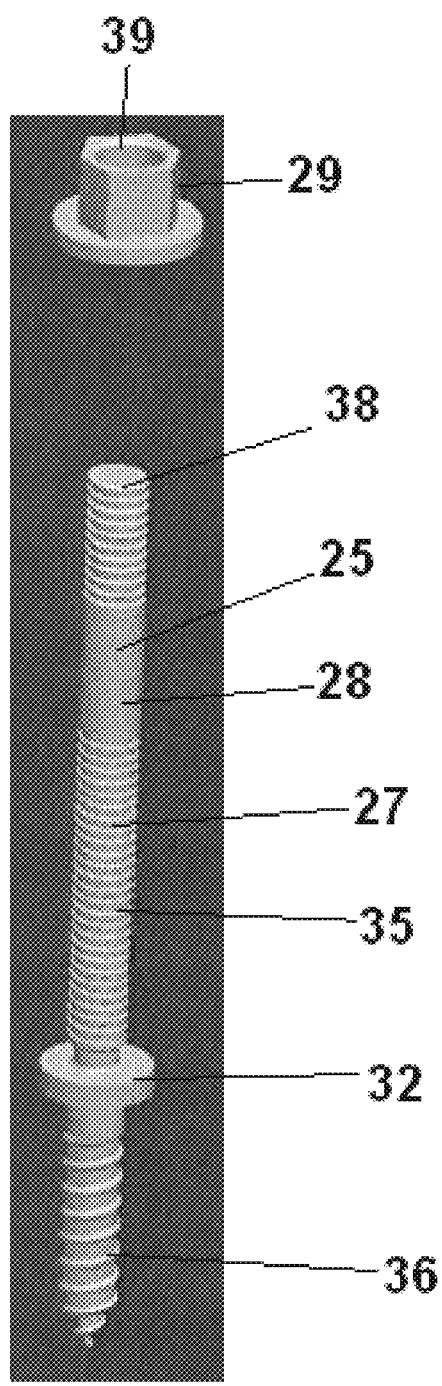
FIG. 7 shows a bone pin in accordance with some embodiments.

In FIG. 4, the bone pin 25 is shown separately from the distraction blade 10. The bone pin 25 is comprised of two different components—a threaded post 27 and a locking nut 29. In some embodiments, the threaded post 27 can have one or more threads that extend along a length of its body. As shown in FIG. 7, the threaded post 27 can have multiple threads with different pitches. These threads will be discussed below. In addition to the threads, the threaded post 27 can have a washer, flange, protrusion or shelf portion 32 on which the ring element 17 of the distraction blade 10 can reside on prior to downwardly threading the locking nut 29. As shown in FIG. 4, the locking nut 29 is a separate component from the threaded post 27, and includes internal threads to thread down the threaded post 27.

Figure 6:
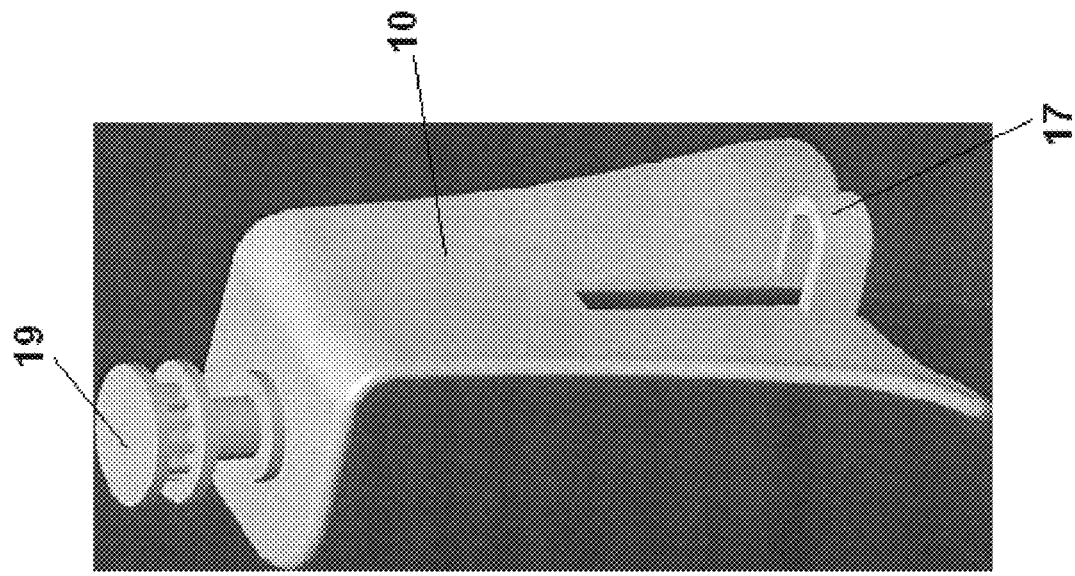
FIG. 6 shows the distraction blade of FIG. 5.
Figure 5:
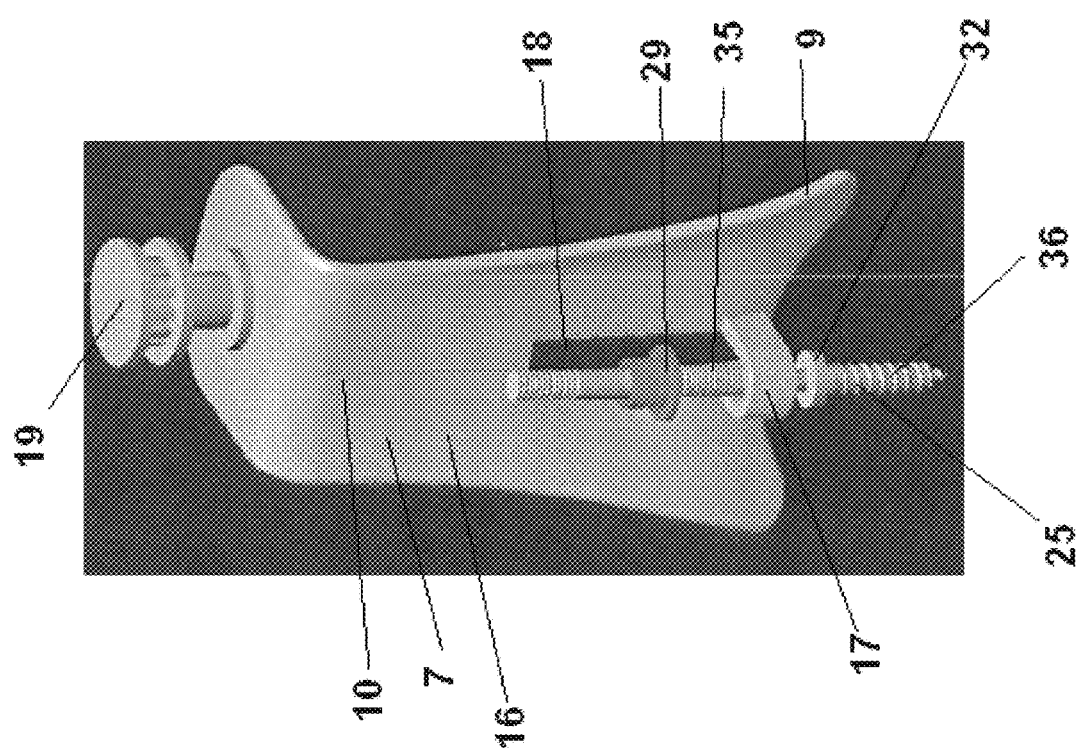
FIG. 5 shows an alternative distraction blade and integrated bone pin in accordance with some embodiments.

FIG. 5 shows an alternative distraction blade and integrated bone pin in accordance with some embodiments, while FIG. 6 just shows the distraction blade. The distraction blade 10 is similar to the blade above and includes a body 16 having an upper flattened portion with an attachment portion 19 extending therefrom; a downwardly flared portion including a slot 18; and a ring element 17 that extends outwardly from the downwardly flared portion. In contrast to the prior embodiment, however, the slot 18 is not flared open, but rather, maintains a continuous width down the length of the distraction blade 10. Regardless of the shape distinction, any of the slots 18 from the different embodiments advantageously allow the distraction blade 10 to be side-loaded if desired onto an inserted bone pin 25. In addition, the distraction blade 10 can also be top-loaded if desired onto an inserted bone pin 25 by, for example, depositing the ring element 17 over the bone pin 25. From these views, one can see the distinct contour of the body 16 of the distraction blade 10. As shown in the figures, starting from the top flattened portion of the distraction blade 10, the body 16 is tapered and flares outwardly such that a distal portion 9 of the distraction blade 10 is wider than a proximal portion 7 of the distraction blade.

FIG. 7 shows a bone pin in accordance with some embodiments. The bone pin 25 can be used with any of the distraction blades described herein. The bone pin 25 comprises two components—a threaded post 27 and a locking nut 29. As shown in FIG. 7, the threaded post 27 comprises an upper section separated from a lower section by flanged shelf portion 32. The lower section of the threaded post 27 includes lower threads 36 to help drive the threaded post 27 into bone. The upper section of the threaded post 27 includes a first set of upper threads 35 and a second set of upper threads 38 separated by a smooth break portion 28. The first set of upper threads 35 is positioned closer to a distal end of the threaded post 27 than the second set of upper threads 38. The first set of upper threads 35 and second set of upper threads 38 are similar threads that enable the locking nut 29 to be downwardly threaded thereon. Advantageously, the first set of upper threads 35 and second set of upper threads 38 are separated by a smooth break 28, which helps the locking nut 29 to be downwardly deposited quicker, as it can easily traverse the smooth break 28 without threading.

As shown in FIG. 7, a locking nut 29 can be downwardly threaded onto the threaded post 29. The locking nut 29 comprises a drive opening 39 for receiving a drive instrument. In some embodiments, the drive opening 39 comprises a hex opening for receiving a hex screw driver.

FIGS. 8A and 8B show different views of a frame in accordance with some embodiments. The frame 50 comprises a first arm 51 for gripping an attachment portion 19 of a first distraction blade 10 and a second arm 52 for gripping an attachment portion 19 of a second distraction blade 10. The frame 10 includes a table mount attachment portion 64 for attaching a table mount thereto. The frame 10 includes a linearly actuating, ratcheting mechanism 65. To actuate the ratcheting mechanism 65, the knob 61 can be rotated (e.g., via optional butterfly key 62). The use of the butterfly key 62 advantageously allows for controlled movement of the ratcheting mechanism 65 in one direction. To move the ratcheting mechanism 65 in an opposite direction, a surgeon can press on the latch 67, which releases from the ratcheting teeth and allows for opposite movement.

With the first distraction blade 10 attached to the first arm 51 and the second distraction blade 10 attached to the second arm 52, the frame 50 is capable of applying a force to separate the first distraction blade 10 from the second distraction blade 10, thereby distraction adjacent vertebral bodies. In some embodiments, two or more frames 50 can be stacked on top of another, to cause an incision side to open in 2, 3, 4 or more directions. In some embodiments, top-loading handheld adaptors can also be provided to retain the distraction blades 10 prior to or after attachment of the frame 50.

Figure 10:
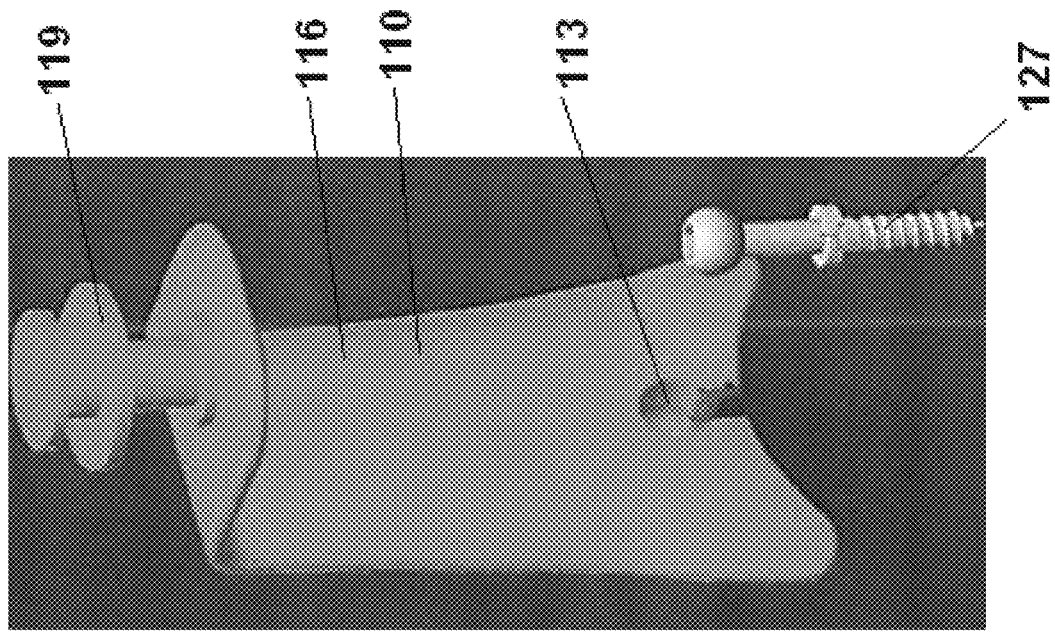
FIG. 10 shows a rear view of a distraction blade having a ball-socket connection with bone pin in accordance with some embodiments.
Figure 9:
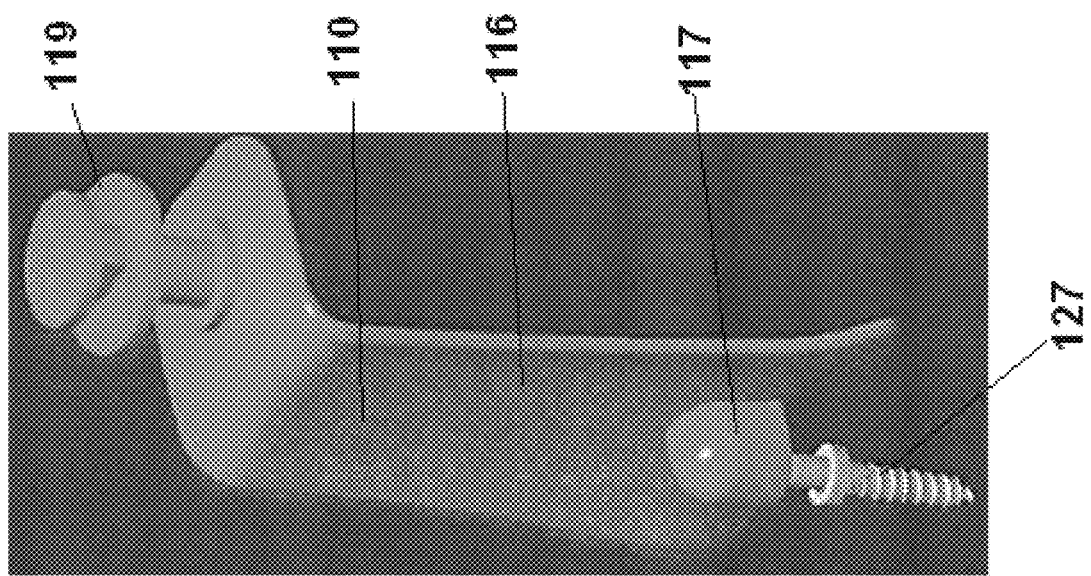
FIG. 9 shows an alternative distraction blade having a ball-socket connection with integrated bone pin in accordance with some embodiments.

FIG. 9 shows an alternative distraction blade having a ball-socket connection with integrated bone pin in accordance with some embodiments. FIG. 10 shows a rear view of the distraction blade. In these embodiments, the distraction blade 110 comprises a body 116 having an upper flattened portion with an attachment portion 119 extending therefrom and a lower sweeping portion. The distal portion of the distraction blade 110 comprises a ball-socket connection 117 for receiving a head of a threaded post 127 therein. In contrast to embodiments in which the distraction blade 10 includes a ring element 17 and a locking nut 29 to secure the blade 10 to the threaded post 27, in the present embodiment, the threaded post 127 can be attached to the ball-socket connection 117 via a snap fit.

As shown in FIG. 10, the threaded post 127, which is shown with a rounder, more spherical head, can be inserted into a rear opening 113 formed in on a backside of the distraction blade 110, to securely snap into the distraction blade 110. Advantageously, as the head of the threaded post 127 is rounded, the distraction blade 110 can be polyaxially adjusted around the threaded post 116, thereby allowing angling and wanding of the blade 110 during distraction and retraction. After inserting a first threaded post 127 into a first vertebral body and a second threaded post 127 into a second vertebral body, a first distraction blade 110 can be snap-fitted to the first threaded post 127, while a second distraction blade 110 can be snap-fitted to the second threaded post 127. With the pair of blades in position, an instrument (e.g., the frame in FIGS. 8A and 8B) can be attached to the blades 110 to advantageously retract tissue and distract bone members using the same instrument.

Figure 12:
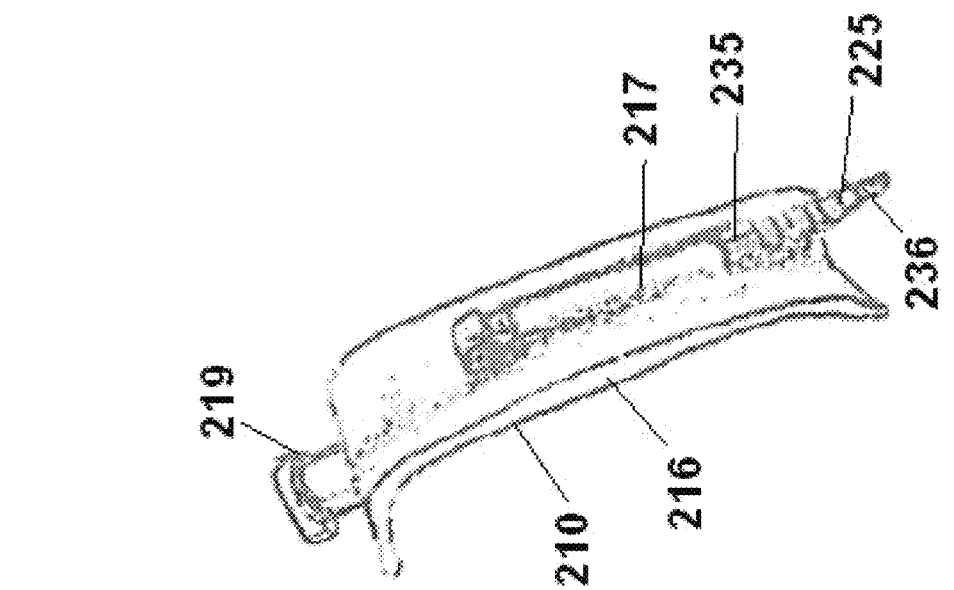
FIG. 12 shows a distraction blade with integrated jointed bone pin in accordance with some embodiments.
Figure 11:
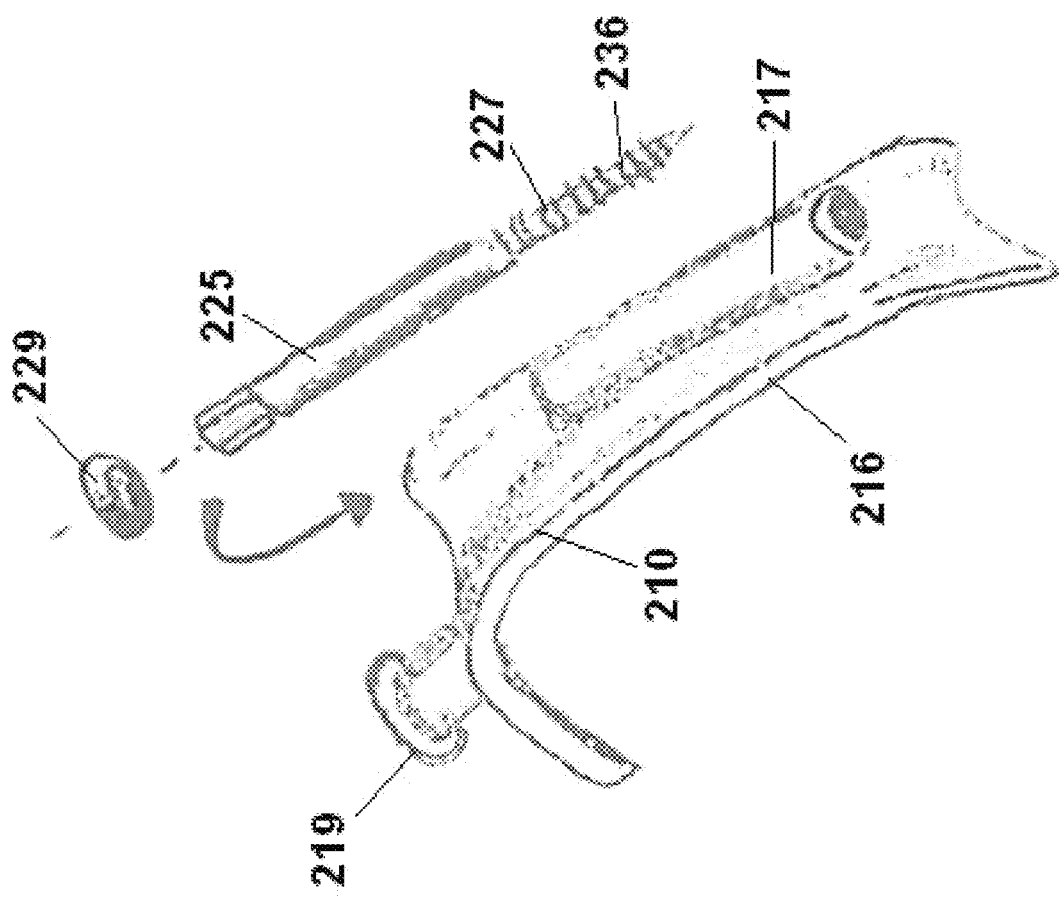
FIG. 11 shows an alternative distraction blade and jointed bone pin in accordance with some embodiments.

FIGS. 11 and 12 shows an alternative distraction blade and jointed bone pin in accordance with some embodiments. The distraction blade 210 comprises a body 216 having an upper portion with an attachment portion 219 extending therefrom and a lower portion that is tapered and flares outwardly. The lower portion of the blade 210 includes a slotted sleeve or shim 217 for receiving a jointed bone pin 225 therethrough.

The jointed bone pin 225 comprises two components—a threaded post 227 and a locking nut 229. The threaded post 227 comprises a distally threaded portion 236 for threading into bone. In a section that is proximal to the distally threaded portion 236, the threaded post 227 advantageously includes a jointed portion 235 that allows the threaded post 227 to bend and angle, even after it has been received through the slotted sleeve 217. In some embodiments, the distraction blade 210 with the slotted shim 217 is top-loaded over the threaded post 227. Once the distraction blade 210 is received over the threaded post 227, the locking nut 229 can be downwardly threaded onto the threaded post 227. The downward threading of the locking nut 229 causes the distraction blade 210 to compress further down the threaded post 227, and secures the distraction blade 210 to the threaded post 227 by preventing backout of the blade 210.

Advantageously, even after the distraction blade 210 is attached to the threaded post 227, the jointed portion 235 allows for angling and wanding of the distraction blade 210, thereby accommodating larger or additional instruments during distraction and retraction. In some embodiments, the distraction blade 210 is capable of angling and wanding until the locking nut is tightly threaded 229 down the threaded post 227. In some embodiments, the slotted shim or sleeve 217 can also be jointed to accommodate angling and wanding of the distraction blade 210. Accordingly, in some embodiments, the threaded post 227 and/or the slotted shim or sleeve 227 can be jointed to accommodate angling or wanding of the distraction blade 210.

As in the embodiments above, the distraction blade 210 can include an attachment portion 219 for attaching to a retraction and/or distraction instrument, such as the frame shown in FIGS. 8A and 8B. In some embodiments, a first distraction blade 210 can be positioned over a first jointed post 227 and a second distraction blade 210 can be positioned over a second jointed post 227. A first locking nut 229 can be downwardly deposited to secure the first distraction blade 210 to the first jointed post 227 in a fixed position, while a second locking nut 229 can be downwardly deposited to secure the second distraction blade 210 to the second jointed post 227. A frame 50 (as shown in FIGS. 8A and 8B) can be attached to each of the first distraction blade 210 and the second distraction blade 210. The frame 50 can be linearly ratcheted, thereby causing the first distraction blade 210 to be pulled away from the second distraction blade 210, hence causing distraction of adjacent vertebral bodies. Advantageously, the blades 210 also retract tissue and maintain an opening for instruments and implants to be inserted between the blades 210 during the surgical process.

As discussed above, surrounding tissue can be injured or damaged during both tissue retraction and bone distraction. While the distraction blades 210 described above are designed to perform both distraction and retraction, thereby reducing the need for additional instruments and increasing visibility of a surgical site to prevent tissue damage, additional protection of surrounding tissues may be desired. To provide additional protection to surrounding tissue, one or more wide blocking blades can be provided. These blades can be used advantageously on their own or with the distraction blades described above to provide protection to surrounding tissue.

Figure 14:
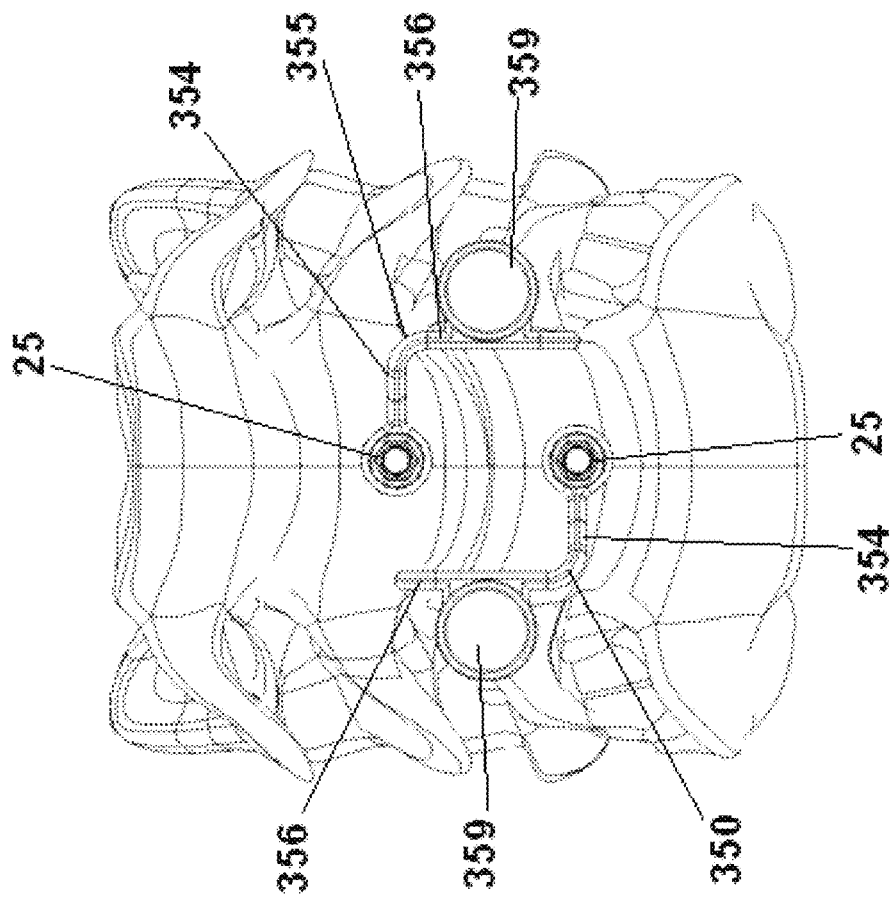
FIG. 14 shows a top view of the system including a pair of wide blocking blades of FIG. 13.
Figure 13:
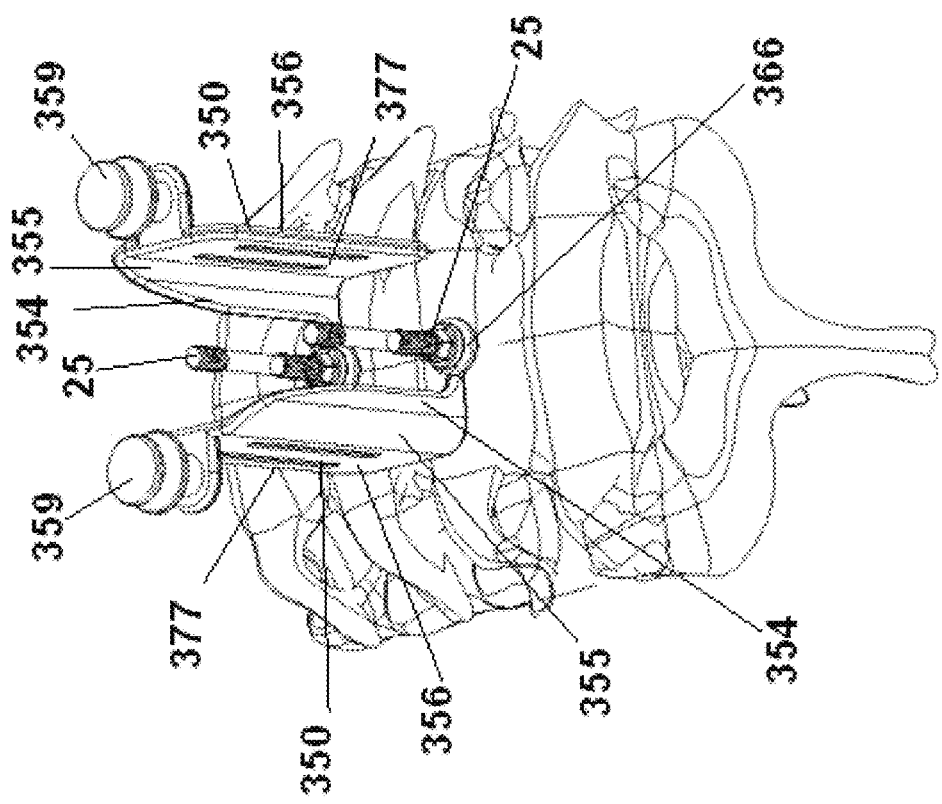
FIG. 13 shows a system including a pair of wide blocking blades in accordance with some embodiments.

FIG. 13 shows a surgical system comprising a pair of wide blocking blades in accordance with some embodiments. FIG. 14 shows a top view of the wide blocking blades. The wide blocking blades 350 advantageously retract tissue and provide protection to surrounding tissue during a surgical procedure, particularly in a medial-to-lateral direction. Advantageously, the wide blocking blades 350 can be attached to the bone pins 25 described above, such that they can be used in conjunction with any of the distraction blades described above.

Figure 15:
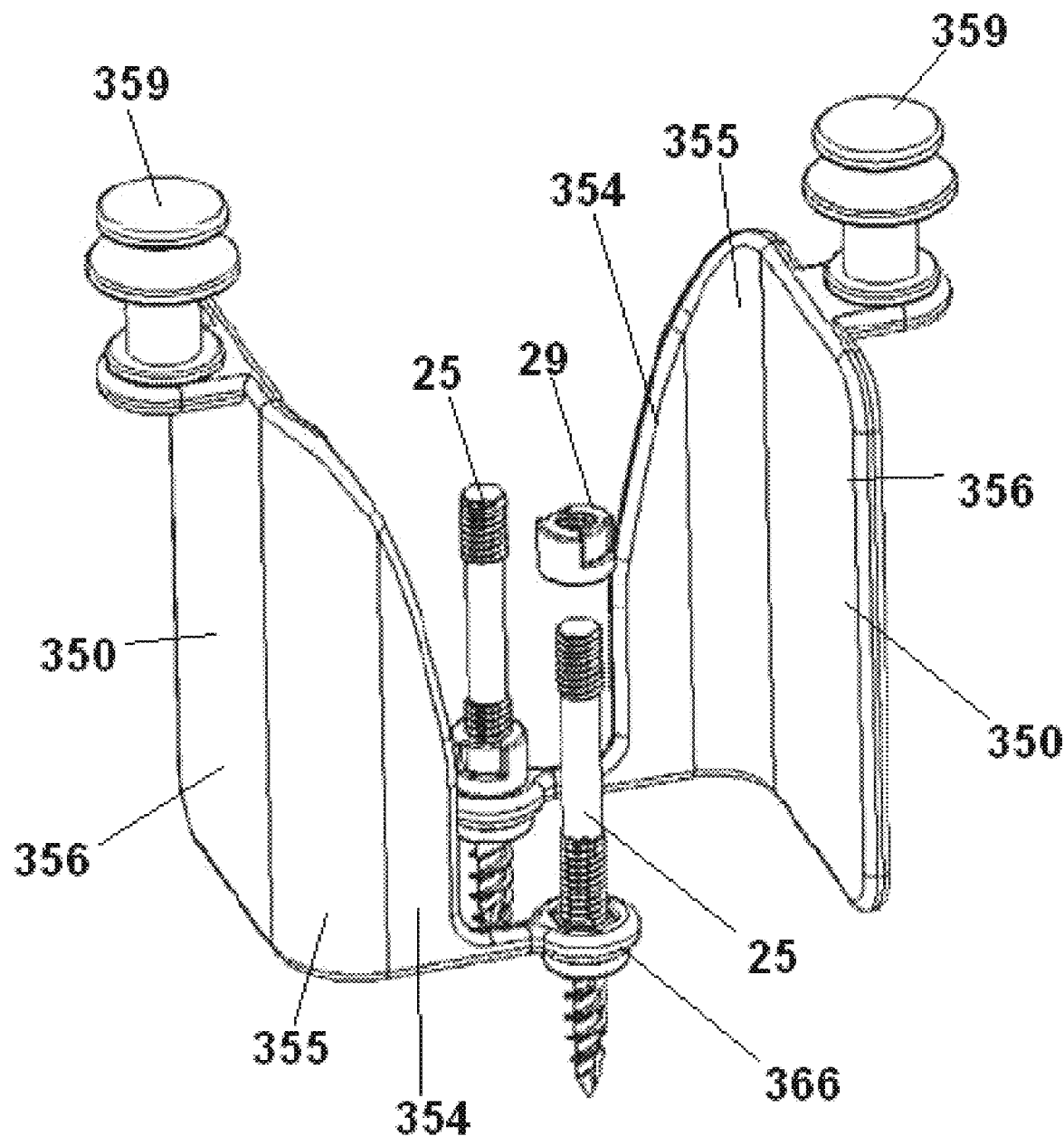
FIG. 15 shows a pair of wide blocking blades in accordance with some embodiments.
Figure 16:
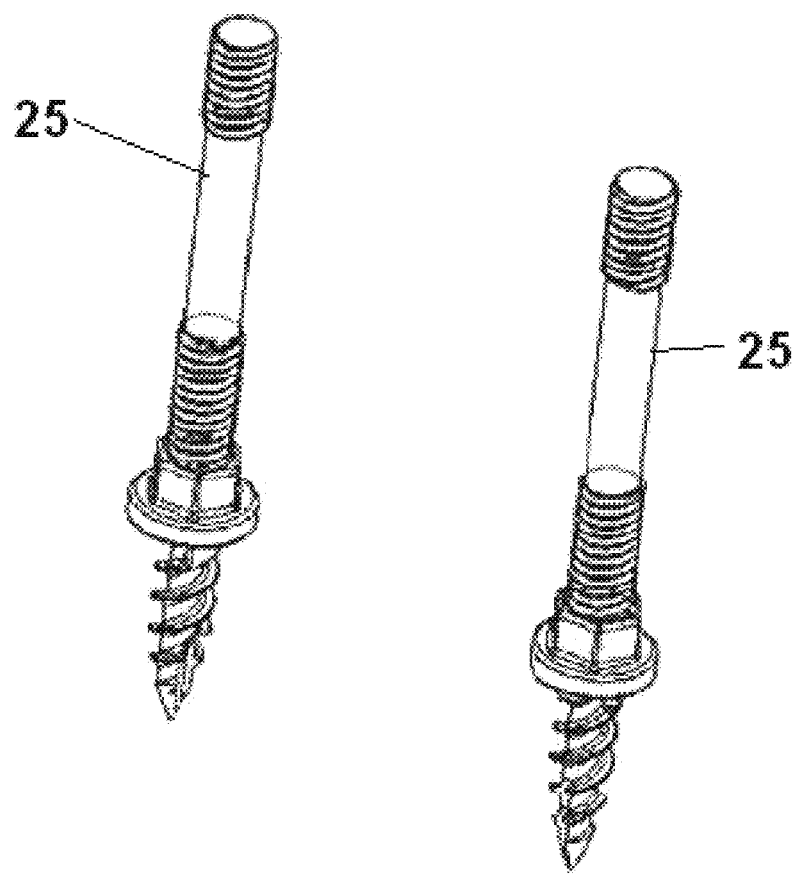

In some embodiments, each of the wide blocking blades 350 comprises a first blocking panel 354, a transition panel 355 and a second blocking panel 356. The first blocking panel 354 comprises a substantially flat wall (shown in FIG. 14) that is attached to a bone pin receiver 366. The bone pin receiver 366 comprises a ring or annular member that is capable of sliding along the shaft of the bone pin 25, until it rests on a shelf portion of the bone pin 25 (as shown in FIG. 15). In the configuration of FIG. 14, the first blocking panel 354 can protect tissue, particularly in the cephalad-to-caudal direction. Adjacent the first blocking panel 354 is a curved transition panel 355. The curved transition panel 355 comprises a curved wall that connects the first blocking panel 354 to the second blocking panel 356. Advantageously, the curved transition panel 355 can also serve as a blocking wall that protects tissue from damage during a surgical procedure. On the other side of the curved transition panel 355 is a second blocking panel 356, which is wider than the first blocking panel 354. In the configuration of FIG. 14, the second blocking panel 356 can protect tissue, particularly in the medial-to-lateral direction. An attachment section 359 for attaching to another instrument (e.g., a frame 50) can be found on an upper surface of the second blocking panel 356.

In some embodiments, one or more of the panels can include openings, windows or fenestrations 377 (shown in FIG. 13 on the second blocking panels 356). These fenestrations 377 are optional and are designed to lessen any potential damage with surrounding tissue. As shown in FIG. 13, the fenestrations 377 can be formed in an up to down direction along the panel walls; however, in other embodiments, the fenestrations can be formed in a sideways direction or in any other shape or pattern.

The wide blocking blades 350 can advantageously be used on their own, or with any of the distraction blades discussed above. A method of assembling one or more wide blocking blades 350 with one or more distraction blades 10 will now be described.

FIG. 15 shows a pair of wide blocking blades in accordance with some embodiments. Each of the wide blocking blades 350 comprise a first blocking panel 354, a transition panel 355 and a second blocking panel 356. A bone pin receiver 366 extends outwardly from the first blocking panel 354. From this view, one can see how the bone pin receiver 366 is slidably received around the bone pin 25 until it resides on a distal portion of the bone pin 25. In some embodiments, the bone pin receivers 366 can be of a certain internal shape (e.g., hexagonal) such that the wide blocking blades 350 do not rotate once they are deposited on the bone pins 25.

FIGS. 16-21 show a method of assembly of a system of one or more wide blocking blades in conjunction with one or more distraction blades in accordance with some embodiments. In some embodiments, a method of assembly of a system of one or more wide blocking blades comprises the following:

(i) Begin by forming a slightly off-midline incision. Using a handheld retractor, retract tissue in the medial-lateral direction.

(ii) Insert first and second bone pins 25 (shown in FIG. 16) into the center of the vertebral body above and below the target disc level. At this point, the locking nuts associated with the bone pins 25 should be removed before inserting the bone pins 25 to enable wide blocking blades and/or distraction blades to be delivered onto the bone pins 25.

(iii) Position a first wide blocking blade 350 over the first bone pin 25 to retract tissue in the medial-to-lateral direction, as shown in FIG. 17. A second wide blocking blade 350 can be positioned over the second bone pin 25 to retract tissue in the medial-to-lateral direction. If no cephalad-to-caudal tissue retraction is required, first and second locking nuts can be threaded down the bone pins 25 to secure the wide blocking blades 350 in place. In some embodiments, if desired, two wide blocking blades 350 can be placed on the same bone pin 25 to retract alternate sides. This can be particularly useful for multi-level ACDFs. Advantageously, no longus muscle dissection is required for the procedure described herein, thereby reducing risk of injury or trauma to a patient.

Figure 19:
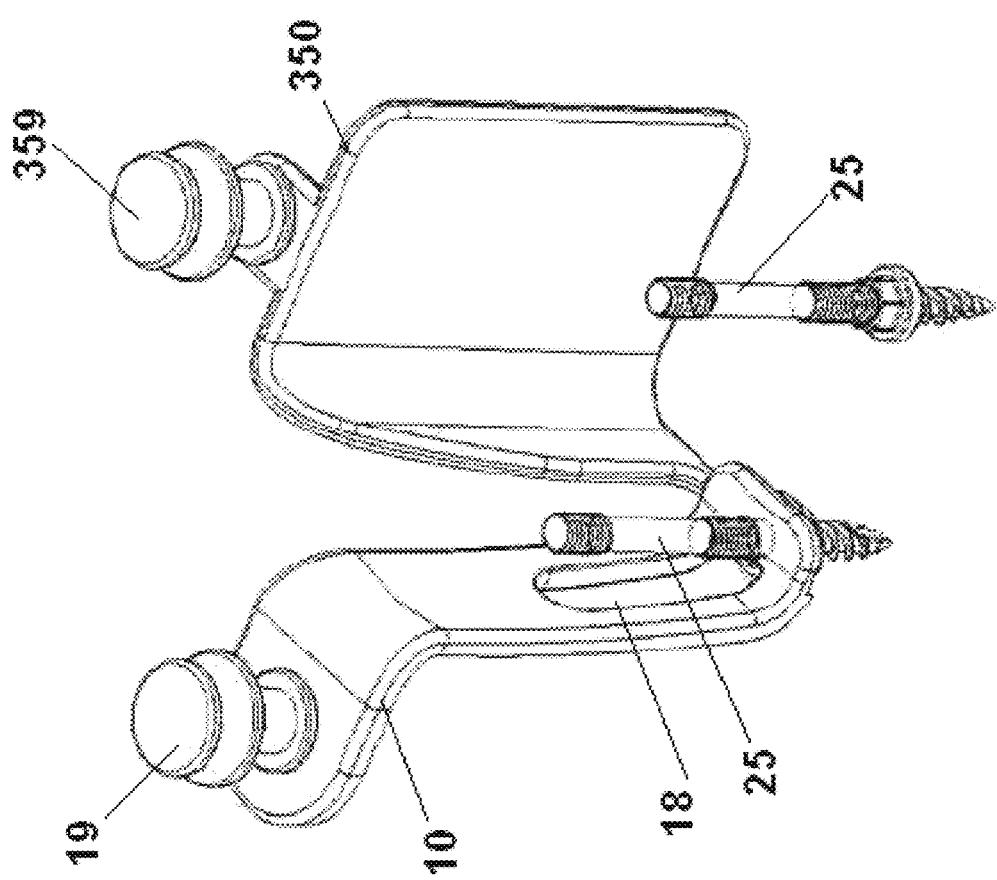

(iv) If desired, a first distraction blade 10 can also be delivered down the first bone pin 25 over the first wide blocking blade 350, as shown in FIG. 19. The distraction blade 10 can be positioned at a different angle from the wide blocking blade 350. While the wide blocking blade 350 can retract tissue in one direction (e.g., in a medial-to-lateral direction), the distraction blade 10 can advantageously retract tissue and assist in bone distraction in a different direction (e.g., in a cephalad-to-caudal direction). The same assembly can be formed with respect to the second bone pin 25, thereby creating a retraction and distraction system with at least four walls.

Figure 20:
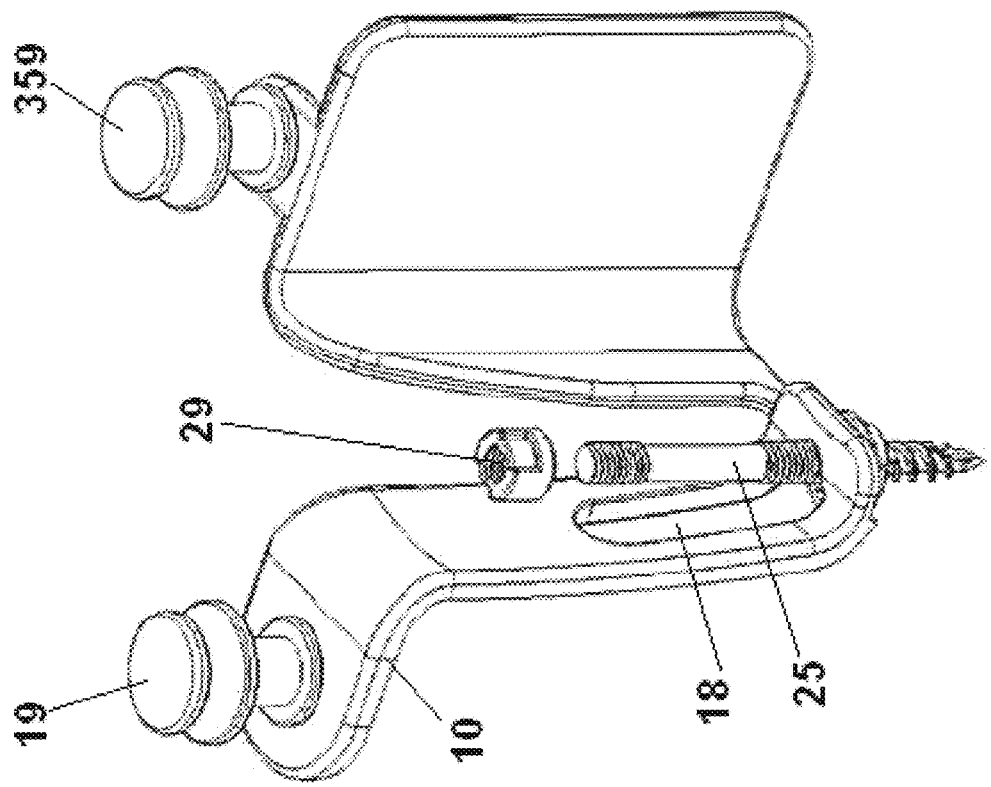
Figure 21:
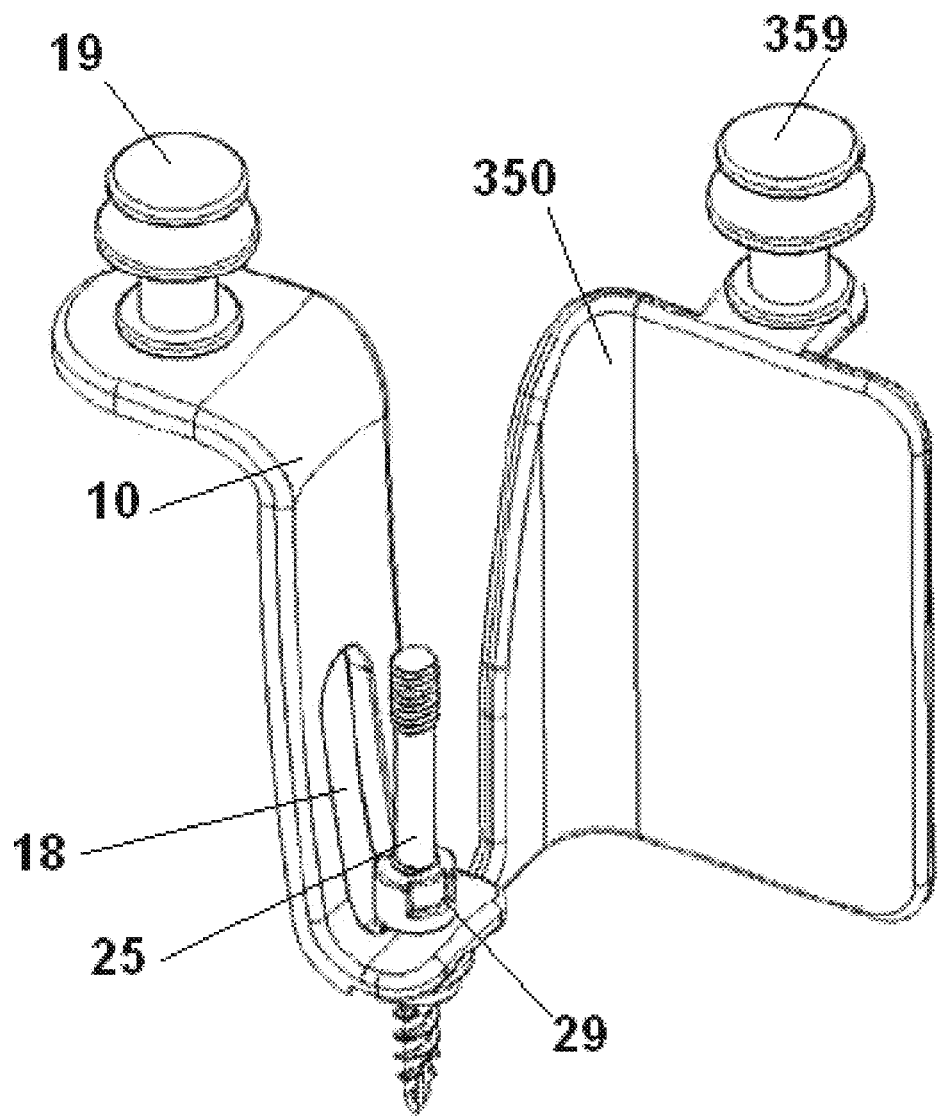

(v) With the distraction blades 10 and wide blocking blades 350 in place over the bone pins 25, locking nuts 29 can be delivered down the bone pins 25 to secure the assemblies, as shown in FIGS. 20-21.

(iv) At this point, one or more frames 50 (as shown in FIGS. 8A and 8B) can be attached to the assembled system of bone pins 25. The one or more frames 50 are capable of distracting vertebrae in one or more directions.

While the embodiments described above show the wide blocking blades 350 in use with one or more distraction blades, in some embodiments, the distraction blades need not be added. FIG. 22 shows a pair of wide blocking blades 350 without the addition of the distraction blades discussed above. The wide blocking blades 350 are connected to a frame 50 which can be used to hold the wide blocking blades 350 apart as needed. This creates a space in between the wide blocking blades 350 for surgical instruments to be inserted therethrough.

The various systems described above, including those that comprise one or more distraction blades and wide blocking blades, can assist in various spinal procedures. In particular, fusion procedures, such as ACDF procedures, can benefit from the use of the systems described above. The systems described above can provide access to surgical sites such that implants, such as cages and spacers (both expandable and non-expandable), as well as graft material, can be inserted with ease. In addition, the systems described above can be used with a number of other implants including, but not limited to, stabilization members (such as rods, hook members and bone screws, including occipital plate systems), prosthetic members (including prosthetic discs), and various other spinal devices.

It will be apparent to those skilled in the art that various modifications and variations can be made in the present invention without departing from the scope or spirit of the invention. Moreover, the improved bone screw assemblies and related methods of use need not feature all of the objects, advantages, features and aspects discussed above. Thus, for example, those skilled in the art will recognize that the invention can be embodied or carried out in a manner that achieves or optimizes one advantage or a group of advantages as taught herein without necessarily achieving other objects or advantages as may be taught or suggested herein. In addition, while a number of variations of the invention have been shown and described in detail, other modifications and methods of use, which are within the scope of this invention, will be readily apparent to those of skill in the art based upon this disclosure. It is contemplated that various combinations or subcombinations of these specific features and aspects of embodiments may be made and still fall within the scope of the invention. Accordingly, it should be understood that various features and aspects of the disclosed embodiments can be combined with or substituted for one another in order to form varying modes of the discussed bone screw assemblies. Thus, it is intended that the present invention cover the modifications and variations of this invention provided that they come within the scope of the appended claims or their equivalents.

What is claimed is:

1. A method of using an orthopedic system with respect to a target disc level of a patient, said method comprising:
   forming an incision in a patient;
   using a handheld retractor to retract tissue of a patient in a first direction;
   assembling the orthopedic system, wherein the orthopedic system comprises:
      a first bone pin, wherein the first bone pin comprises a lower threaded portion and an upper threaded portion;
      a first wide blocking blade configured to be delivered over the first bone pin, wherein the first wide blocking blade comprises at least two blocking panels;
      a first distraction blade configured to be delivered over the first bone pin, wherein the first distraction blade includes a slot for receiving the first bone pin therein;
      a second bone pin, wherein the second bone pin comprises a lower threaded portion and an upper threaded portion;
      a second wide blocking blade configured to be delivered over the second bone pin, wherein the second wide blocking blade comprises at least two blocking panels;
      a second distraction blade configured to be delivered over the second bone pin, wherein the second distraction blade includes a slot for receiving the second bone pin therein; and
      a frame configured to attach to at least one of either: (i) the first distraction blade and the second distraction blade or (ii) the first wide blocking blade and the second wide blocking blade;
   wherein assembling further comprises:
      inserting the first bone pin into a first vertebral body above the target disc level;
      inserting the second bone pin into a second vertebral body below the target disc level;
      positioning the first wide blocking blade over the first bone pin and retracting tissue in the first direction;
      positioning the second wide blocking blade over the second bone pin and retracting tissue in in the first direction;
      delivering the first distraction blade down the first bone pin over the first wide blocking blade;
      delivering the second distraction blade down the second bone pin over the second wide blocking blade;
      retracting tissue in a second direction using the first distraction blade and the second distraction blade; and
      attaching the frame to the first bone pin and the second bone pin.

2. The method of claim 1, wherein the frame comprises a ratcheting mechanism.

3. The method of claim 1, wherein the first bone pin comprises a shelf portion that separates the lower threaded portion from the upper threaded portion.

4. The method of claim 1, wherein the first wide blocking blade comprises a first panel, a second panel and a transition panel between the first panel and the second panel.

5. The method of claim 4, wherein the transition panel is curved.

6. The method of claim 1, wherein the first distraction blade has a flared out, curved contour.

7. The method of claim 1, wherein the first distraction blade has an attachment portion, wherein the attachment portion is connectable to the frame.

8. The method of claim 1, wherein the first distraction blade comprises a flattened upper section that transitions downwardly into a flared section.

9. A method of using an orthopedic system with respect to a target disc level of a patient, said method comprising:
   forming an incision in a patient;
   using a handheld retractor to retract tissue of a patient in a first direction;
   assembling the orthopedic system, wherein the orthopedic system comprises:
      a first bone pin;
      a first wide blocking blade configured to be delivered over the first bone pin;
      a first distraction blade configured to be delivered over the first bone pin, wherein the first distraction blade includes a slot for receiving the first bone pin therein;
      a second bone pin;
      a second wide blocking blade configured to be delivered over the second bone pin;
      a second distraction blade configured to be delivered over the second bone pin, wherein the second distraction blade includes a slot for receiving the second bone pin therein; and
      a frame configured to attach to at least one of either: (i) the first distraction blade and the second distraction blade or (ii) the first wide blocking blade and the second wide blocking blade;
   wherein assembling further comprises:
      inserting the first bone pin into a first vertebral body above the target disc level;
      inserting the second bone pin into a second vertebral body below the target disc level;
      positioning the first wide blocking blade over the first bone pin and retracting tissue in the medial-lateral direction;
      positioning the second wide blocking blade over the second bone pin and retracting tissue in in the medial-lateral direction;
      delivering the first distraction blade down the first bone pin over the first wide blocking blade;
      delivering the second distraction blade down the second bone pin over the second wide blocking blade;
      retracting tissue in a second direction using the first distraction blade and the second distraction blade; and
      attaching the frame to the first bone pin and the second bone pin.

10. The method of claim 9, wherein the slot in the first distraction blade is tapered.

11. The method of claim 9, wherein the first bone pin comprises a set of upper threads and a set of lower threads.

12. The method of claim 11, wherein the pitch of the upper threads is different from the pitch of the lower threads.

13. The method of claim 11, wherein the first wide blocking blade comprises at least two panels.

14. The method of claim 13, wherein the first wide blocking blade comprises a first panel separated from a second panel by a transition panel.

15. The method of claim 9, wherein the slot of the first distraction blade is part of a shim.

16. The method of claim 15, wherein the first bone pin is a jointed bone pin.

17. A method of using an orthopedic system with respect to a target disc level of a patient, said method comprising:
   forming an incision in a patient;
   using a handheld retractor to retract tissue of a patient in a first direction;
   assembling the orthopedic system, wherein the orthopedic system comprises:
      a first bone pin;
      a first wide blocking blade configured to be delivered over the first bone pin;
      a second bone pin;
      a second wide blocking blade configured to be delivered over the second bone pin; and
      a frame attached to the first wide blocking blade and the second wide blocking blade;
   wherein assembling further comprises:
      inserting the first bone pin into a first vertebral body above the target disc level;
      inserting the second bone pin into a second vertebral body below the target disc level;
      positioning the first wide blocking blade over the first bone pin and retracting tissue in the first direction;
      positioning the second wide blocking blade over the second bone pin and retracting tissue in in the first direction;
      delivering the first distraction blade down the first bone pin over the first wide blocking blade;
      delivering the second distraction blade down the second bone pin over the second wide blocking blade;
      retracting tissue in a second direction using the first distraction blade and the second distraction blade; and
      attaching the frame to the first bone pin and the second bone pin.

18. The method of claim 17, wherein the first wide blocking blade comprises a first blocking panel and a second blocking panel.

19. The method of claim 18, wherein the first blocking panel is on a different plane from the second blocking panel.

20. The method of claim 19, further comprising a first distraction blade attached to the first bone pin and a second distraction blade attached to the second bone pin.

* * * * *